United States Patent [19]

Dawson, Jr.

[11] 4,029,090
[45] June 14, 1977

[54] HORSE FORELEG BRACE

[76] Inventor: Garrett W. Dawson, Jr., Triple D Farm (Box 187 A), Greensboro, Md. 21639

[22] Filed: July 26, 1976

[21] Appl. No.: 708,744

[52] U.S. Cl. .............................. 128/87 R; 128/88; 54/82

[51] Int. Cl.² .......................................... A61F 5/04

[58] Field of Search ............ 128/82, 83, 85, 87 R, 128/88, 89; 54/82, 65; 119/143, 145

[56] References Cited

UNITED STATES PATENTS

| 739,634 | 9/1903 | Allen | 128/87 R |
|---|---|---|---|
| 2,016,958 | 10/1935 | Clarke | 128/87 R |
| 3,416,519 | 12/1968 | Dowers | 128/87 R |
| 3,470,873 | 10/1969 | Walker et al. | 128/85 |
| 3,913,302 | 10/1975 | Centers | 54/82 X |

Primary Examiner—John D. Yasko
Attorney, Agent, or Firm—Abramo & Abramo

[57] ABSTRACT

The horse foreleg brace is a cylindrical framework having hinges along the outside of the brace for opening and closing the cylinder of the leg brace and a restraining means on the other side to keep the brace closed. The top of the brace is an irregular oval, which engages the shoulder of a horse. The brace is a framework of metal rods wherein metal rods forming a circle are spaced at intervals along the vertical axis of the brace and welded to vertical rods extending downwardly from the shoulder engaging loop. A plate covers the bottom of the brace. The apparatus also has a provision for adjustment to varying lengths of a horse's leg. The apparatus is attached to a horse by means of straps which go across the horse's back and hold the apparatus in place. It is suitable for use with all four-legged animals.

6 Claims, 6 Drawing Figures

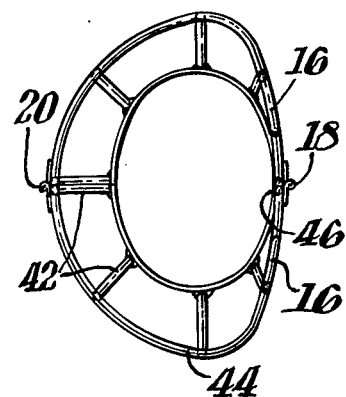
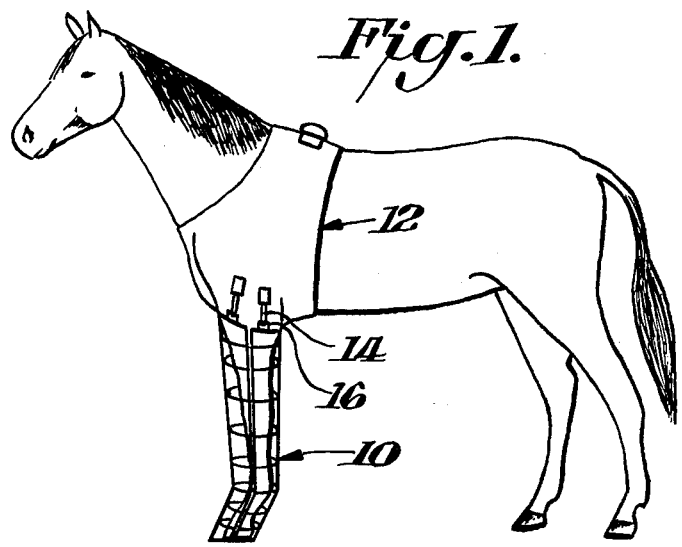
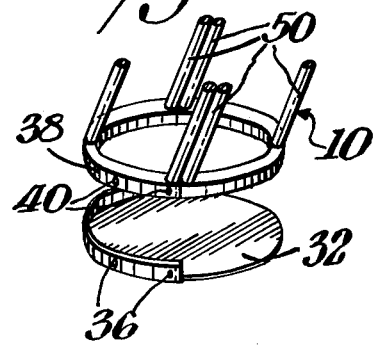
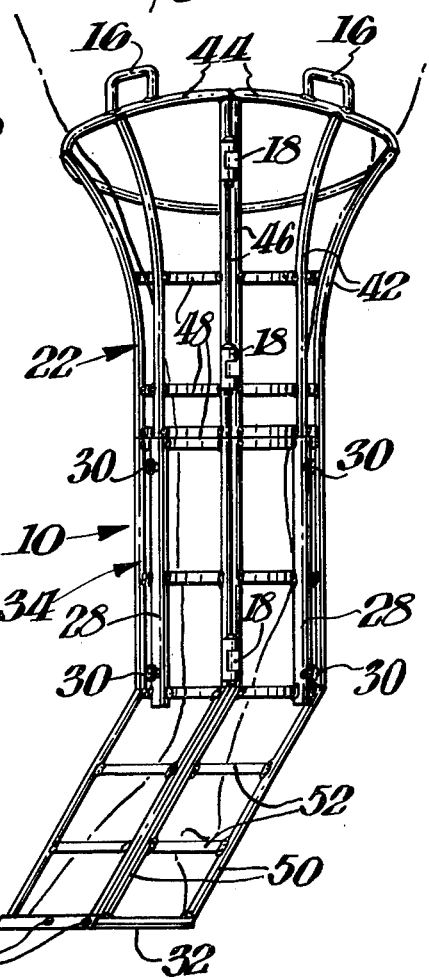
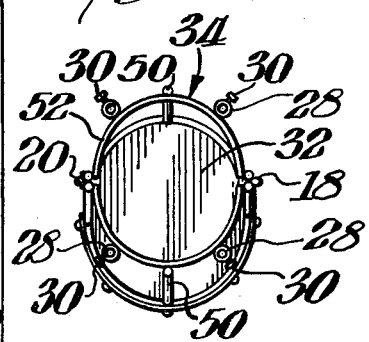

HORSE FORELEG BRACE

FIELD OF THE INVENTION

The present invention relates to an animal leg brace particularly for use with the foreleg of quadrupeds. The brace is employed to take the weight off of an injured foreleg of an animal. At the same time, the animal is able to maneuver by lifting the leg brace and striding with it.

DESCRIPTION OF THE PRIOR ART

The problems presented when a valuable horse injures a leg or breaks a foreleg are very great. Frequently, attempts to save the horse are unsuccessful, because the horse is too easily agitated and experiences great pain and suffering. Frequently, the horse must be destroyed.

A variety of suggested solutions to the problem have been tried. Among these are: casts on broken leg, bone grafts, or the bones are held together with metal screws. Another procedure followed involves amputation of a part of the broken leg and replacing it with a prosthetic front leg. Usually, these are not successful because the horse cannot be restrained while the healing process is going on.

Even when a cast has been successfully applied, other problems remain. For example, after a broken bone has been secured by metal screws and a cast applied, the horse will often break the cast or damage the leg again.

A number of devices, which might provide a solution to this problem, have been described in the prior art; however, they all are deemed inadequate solutions. In U.S. Pat. No. 739,634 issued to N. P. Allen, Sept. 22, 1903, a leg brace is described which is made up of a number of wooden or metal slats held together by a series of belts. In use, the device is wrapped around an injured animal's leg, and the belts are cinched up to hold the brace in position. The brace is designed to be longer than the animal's leg so that the weight of the animal is borne on the end of the slats. This device is not an acceptable solution because it could not function in the presence of a cast on an animal's leg. As the design of the Allen apparatus shows, it is designed to be strapped tightly to the upper foreleg or below the knee of a horse. In neither case is there room for a cast underneath the leg brace. In addition, the device would cut off circulation of blood by pressing against the veins in the horse's leg. The Allen device does not allow for the curvative of the lower portion of the horse's leg. The hoof of the horse extends beyond the diameter of the cylinder described by the leg brace. The Allen device avoids this problem by removing one of the slats. However, removing one of the slats would expose the hoof so that it could be hit or twisted and reinjure the leg.

Another device is described in U.S. Pat. No. 874,446 issued to S. C. Slater, Dec. 24, 1907. The Slater patent discloses a device with two adjustable tubular rods which fit along the outside of a human leg and are attached at their top to a circular loop which fits around the upper leg of the wearer. The apparatus is also held in place by a belt attached above the circular loop. The device has a piece of canvas attached between the tubes to support the leg of the person using it. The Slater device is not satisfactory for use with a horse because it is obviously directed to use by humans and is at most a temporary splint for use immediately after someone was injured. It would not be compatible with a cast, and even if it could be made compatible, it would not screen the cast or injured leg from impacts from the front or back.

U.S. Pat. No. 2,016,958 issued to F. Clarke, Oct. 8, 1935, describes a splint to be used by animals which involves a pair of support members attached to a circular loop, which goes around the injured leg of an animal. The device is to be used as a crutch, and in use, the lower end of the animal is to be taped or fixed to the bottom of the apparatus by some restraining means. The device has been used for the gradual alignment of the broken bone of an animal over a period of time. The device is used because it is undesirable to put the animal's bone into its correct position at one setting. Thus, the Clarke device is not intended to be used with a cast and is in fact a crutch to be used in the healing of a broken bone, particularly for a dog. It does not shield the animal's leg from impacts from the side.

U.S. Pat. No. 3,470,873 issued Oct. 7, 1969, to B. F. Walker, et al., describes an adjustable animal splint which is to be used on the hind leg of a large animal, usually cattle. The device uses a loop which passes around the animal's leg and engages the animal's hip, and thereafter, a support member is attached. The support member carries the weight of the animal, and it is provided that the plate to which the hoof is attached is pivotable so that the hoof can be moved. In use, when a broken bone is involved, a cast is applied on the exterior and encases the Walker, et al., device. This device does not operate as a brace or protective device but is in fact a splint, and accordingly, operates on a different principle than a protective brace. It does not protect an injured leg from impacts and is designed for a rear leg.

BRIEF SUMMARY OF THE INVENTION

The present invention is designed to overcome many disadvantages in the prior art devices. The brace is a framework of vertical rod members fastened to horizontal circular rod or band members. Substantially, all of the vertical rod members are curved at the top and are attached to an irregular oval rod member which engages the shoulder of a horse. The brace tapers as it extends downwardly and follows the conformation of the horse's foreleg. The topmost irregular oval is fixed at an acute angle with regard to the vertical rod members, so that it conforms to the shoulder of the horse.

The bottom section of the apparatus is offset so that it conforms to the lower leg and hoof of a horse.

The length of the apparatus is adjusted or selected to be of a length so that the hoof of the horse either rests lightly on a plate fixed to the bottom of the apparatus or is suspended slightly above it.

The framework is spaced one to two inches around the foreleg of the horse so that one to two inches of padding or a cast may be placed around the horse's leg and still provide space for the horse's leg within the framework.

The apparatus is applied to an injured foreleg of the horse by opening the apparatus by means of the hinges fixed to the brace, which allows the brace to be opened along its vertical axis, and then placing it around the injured leg and closing it by means of latch means. The length of the brace should be such that when the apparatus is snug against the shoulder of a horse, the bottom plate of the brace extends just beyond the hoof of the horse. In this way, the weight of the horse is kept off of the injured leg.

In one embodiment the length of the brace is fixed by adjustable means which involve the vertical rod members telescoping into tubular rod members. Once the proper length has been set on the apparatus, the size of the apparatus is fixed by means of set screws in the tubular rod members.

In another embodiment of the invention, a means for examining or treating the hoof area of a horse is provided by a provision for a removable base plate on the brace. The base plate may be taken off for inspection or application of medication or other adjustments which might be desirable. The base plate can be put on or taken off by a fastening means such as screws.

BRIEF DESCRIPTION OF THE DRAWINGS

FIG. 1 is a pictorial view showing the horse foreleg brace in place mounted upon the leg of a horse;

FIG. 2 is a side elevational view of the leg brace showing the foreleg of the horse in phantom outline inside the brace.

FIG. 3 is a front exploded view of the horse leg brace showing the upper section of the leg brace removed from the lower section and illustrating the means by which the leg brace is adjusted to different lengths of the horse's leg and also showing how the brace can be adapted to the right or left foreleg of a horse merely by turning the top section 180°.

FIG. 4 is a top plan view of the upper section of the leg brace.

FIG. 5 is a top plan view of the lower section taken substantially along FIG. 5 to FIG. 2 looking in the direction of the arrows.

FIG. 6 is a fragmental exploded view of the lower section of the horse leg brace showing a detachable hoof plate.

DETAILED DESCRIPTION OF THE INVENTION

Referring now to the drawings, wherein the reference characters designate corresponding parts throughout the several views, FIG. 1 shows the horse foreleg brace 10 in use on a horse's left foreleg. A harness 12 covers the shoulder and back of the horse, and straps 14 on the harness 12 are threaded through loops 16 placed on the top of the leg brace.

Referring to FIG. 2, FIG. 3, and FIG. 4, other features of the horse leg brace 10 are evident. The leg brace is opened prior to being placed around a horse's foreleg by means of the hinges 18. After placing the brace around a horse's leg, it is closed and retained in the closed position with the latches 20, which is diametrically opposed to hinges 18.

FIG. 3 shows the leg brace with its upper section 22 removed from the lower section 24 of the leg brace. The upper section 22 has four extended vertical rods 26 which fit into the four tubular rods 28 and are held in a fixed position by means of set screws 30 in the tubular rod 28. The foreleg brace 10 may be adjusted to any height by setting the upper section 22 a desired height above the lower section 24 and tightening the set screws 30 on the extended vertical rods 26 in the tubular rods 28. The leg brace may also be used with either the left or right foreleg of a horse by turning the upper section 22 about its vertical axis and positioning it over the lower section 24. For example, as shown in FIG. 2 and FIG. 3, the brace is set up for use with the left leg of a horse. By turning the upper section 22 180° with reference to the lower 24, the leg brace can be used with the right leg of a horse.

Another feature of the brace is shown with FIG. 2 and FIG. 5. This feature involves offsetting the bottom portion of the lower section 24 so that it accommodates a horse's lower foreleg which is offset with respect to the rest of a horse's foreleg. The angle of this offset on the brace is approximately the same as the angle that the lower leg of a horse forms with the upper leg.

FIG. 6, FIG. 2, and FIG. 3 show a removable bottom plate 32 which is attached to the bottom of the leg brace 10 by means of screws 34 which fit into the opening 36 and are attached to the front side of the last semicircular band 38 through the openings therein 40.

The upper section 22 is formed from vertical rods 42 which have arcuate portions which curve to meet the topmost band 44 which is formed from approximately equal sized semicircular sections. The top band 44 is an irregular oval which conforms to the shoulder of a horse. The angle $\alpha$ is approximately 25° and may range from 20° to 30° as desired. The vertical rods 46 to which the hinges 18 are attached are substantially straight. The horizontal bands 48 are made up of semicircular sections which are welded to the vertical rods 26, 42, and 48.

The lower section 24 is likewise made up of vertical rods 50 which are deflected at their lower end to as previously mentioned so that the brace will follow the contour of the lower part of a horse's leg. The vertical rods 50 are welded to horizontal bands 52 made up of semicircular sections.

The apparatus is constructed of metal rods welded together to form a cylindrical framework. It is apparent that the top of the framework must be shaped so that it will accomodate the shoulder of the animal on which it is to be applied. The metal rods may be of any suitable material including aluminum, iron, steel, etc. Welding is the usual means of putting the apparatus together. Fiberglass or other non-metal materials of construction can also be used. In some instances a lighter weight apparatus will be advantageous and the lighter fiberglass would be indicated.

In use, the apparatus requires some padding around the area where the brace engages the shoulder of the animal. Foam rubber or fabric batting is suitable for this purpose. It may be also desirable to include some padding around the leg of the animal. Thus, the diameter of the cylindrical framework must be such that it can accommodate padding between it and the horse's leg of approximately one to two inches in thickness.

The brace is designed to be used with a variety of injuries. These will include instances when a horse's leg is broken and a cast has been applied to the injured area. The apparatus is set so that it extends just beyond the length of the horse's leg so that the brace takes the full weight of the horse. Of course, in instances when injury is of a minor nature, it will not be necessary to apply a cast, and the apparatus can be used then merely to keep the horse from aggravating a minor injury.

The apparatus is also an aid to shipping horses. It is known that horses are often injured during shipping. It is frequently necessary to bandage a horse during shipping, and frequently, this does not prevent injury. Application of two leg braces to the forelegs of the horse prior to shipment will prevent many of the common injuries to the horse's legs during shipment.

The apparatus appears to have a quieting influence on a horse. The horse is aware that he cannot maneuver with the same freedom that he had prior to placing the brace on his leg. In addition, when he strides on the side where the brace is placed, he must lift the apparatus in order to move. Thus, his movements are much more restrained than they would normally be, and this has the beneficial effect of preventing the horse from injuring the leg more seriously.

Other embodiments of this invention are also possible, such as a brace which is a rigid framework which conforms to the contour of a horse's leg but which is not hinged to be opened or to be adjusted. However, this apparatus would not be as convenient as the embodiment which can be opened and placed around a leg.

A very important feature of the apparatus is that the entire leg is encased in a metal framework which protects the entire leg. Thus, the hoof is not exposed and cannot be twisted, causing injury to the leg, and any other area which is injured along the full length of the leg is shielded by the framework so that any injury is not aggravated.

The adjustment feature is a desirable feature to have since the legs of horses vary, and it is necessary to be able to place the apparatus at the proper length so that the horse's leg has all weight taken off of it. In addition, in other instances, it may be desirable for a small amount of weight to be borne by the hoof, and the apparatus can be adjusted to accomplish this end.

The removable bottom plate allows access to the horse's hoof thereby providing an opening whereby medication and/or other treatment may be applied to the lower part of the horse's leg.

While this apparatus has been described primarily with regard to its use on a horse, it is apparent that it could also be adapted to use with other animals, such as cattle or small pets. Some modifications in the apparatus would have to be made in order for it to be used in other animals, such as the offset at the lower part of the apparatus would not have to be as severe for a dog or some of the other quadrupeds as it is for a horse.

I claim:
1. A weight bearing foreleg brace for a quadruped for keeping weight off an injured foreleg comprising:
   a. a framework of circumferentially arranged vertical rod members shaped to correspond to the silhouette of a quadruped foreleg and foot, extending from the shoulder to beneath the foot of the quadruped;
   b. horizontal ring members, said ring members being spaced vertically between the shoulder and the foot, each ring member encircles the corresponding portion of the foreleg, each ring member being attached to the vertical rod members by fastening means, said ring members including an uppermost ring member adapted to engage the shoulder of the quadruped and support the weight of the quadruped, each ring member being adapted to open and close for placement or removal of the brace from said foreleg;
   c. hinge means deposed vertically on the periphery of the brace to allow ring members to open and close;
   d. latch means deposed vertically on the periphery of the brace to hold the brace in the closed position after it has been placed on a foreleg; and
   e. plate means attached to the bottom ring member to close the bottom of the brace.

2. A brace as in claim 1 wherein the hinge means are mounted on two adjacent vertical rod members to allow said brace to be alternatively opened and closed.

3. A brace as in claim 1 wherein the latch means are mounted on two adjacent vertical rod members.

4. A brace as in claim 1 wherein the vertical rod members are operably associated with adjustment means whereby the brace can be adjusted to a desired length.

5. A brace as in claim 1 wherein the bottom plate is attached to the brace by removable fastening means whereby the plate may be taken off.

6. A brace as in claim 1 wherein the brace is made of steel rods welded together.

* * * * *